United States Patent
Voigt et al.

(10) Patent No.: US 9,474,715 B2
(45) Date of Patent: Oct. 25, 2016

(54) POLYMERIC DRUG-DELIVERY MATERIAL, METHOD FOR MANUFACTURING THEREOF AND METHOD FOR DELIVERY OF A DRUG-DELIVERY COMPOSITION

(76) Inventors: Andreas Voigt, Berlin (DE); Jörg Kriwanek, Berlin (DE); Scott Hampton, Cumming, GA (US); Andreas Reiff, San Marino, CA (US); Sonja Ludwig, Berlin (DE)

(*) Notice: Subject to any disclaimer, the term of this patent is extended or adjusted under 35 U.S.C. 154(b) by 0 days.

(21) Appl. No.: 13/307,474

(22) Filed: Nov. 30, 2011

(65) Prior Publication Data

US 2013/0136774 A1   May 30, 2013

(51) Int. Cl.
| | |
|---|---|
| A61K 9/06 | (2006.01) |
| A61K 47/30 | (2006.01) |
| A61K 47/36 | (2006.01) |
| A61K 47/38 | (2006.01) |
| A61K 47/42 | (2006.01) |
| A61K 9/50 | (2006.01) |

(52) U.S. Cl.
CPC .............. *A61K 9/06* (2013.01); *A61K 9/5036* (2013.01); *A61K 47/36* (2013.01); *A61K 47/38* (2013.01); *A61K 47/42* (2013.01)

(58) Field of Classification Search
CPC . A61K 9/0014; A61K 45/06; A61K 2300/00
USPC ....................................................... 424/400
See application file for complete search history.

(56) References Cited

U.S. PATENT DOCUMENTS

| | | | |
|---|---|---|---|
| 1,540,979 A | 6/1925 | Bloom | |
| 5,674,495 A | 10/1997 | Bowersock et al. | |
| 5,780,028 A * | 7/1998 | Graham | 424/130.1 |
| 5,876,754 A | 3/1999 | Wunderlich et al. | |
| 6,036,974 A * | 3/2000 | Tsushima et al. | 424/464 |
| 6,280,983 B1 | 8/2001 | Backlund et al. | |
| 6,355,272 B1 | 3/2002 | Caramella et al. | |
| 6,632,671 B2 * | 10/2003 | Unger | 435/455 |
| 2002/0160982 A1 | 10/2002 | Jacobs et al. | |
| 2007/0059336 A1 | 3/2007 | Hughes et al. | |
| 2008/0107694 A1 | 5/2008 | Trogden et al. | |

FOREIGN PATENT DOCUMENTS

| | | |
|---|---|---|
| WO | WO 02/058735 A1 | 8/2002 |
| WO | WO 2006/018119 A1 | 2/2006 |
| WO | WO 2006/057859 A1 | 6/2006 |
| WO | WO 2007/145618 A1 | 12/2007 |
| WO | WO 2010/089104 A2 | 8/2010 |

OTHER PUBLICATIONS

Watano et al., "Development of a Novel Vertical High Shear Kneader and Its Performance in Wet Kneading of Pharmaceutical Powders", Mar. 2002, Chem. Pharm. Bull., 50(3), pp. 341-345.*
Folttmann et al., "Polyvinylpyrrolidone (PVP)—One of the Most Widely Used Excipients in Pharmaceuticals: An Overview", Jun. 2008, Drug Delivery Technology, vol. 8, No. 6, pp. 22-27.*
Aburahma et al., "Preparation and In vitro/In Vivo Characterization of Porous Sublingual Tablets Containing Ternary Kneaded Solid System of Vinpocetine with β-Cyclodextrin and Hydroxy Acid", Sci. Pharm., 78: 363-379 (2010).
de Azevedo et al., "New formulation of an old drug in hypertension treatment: the sustained release of captopril from cyclodextrin nanoparticles", Int. J. of Nanomedicine, 6: 1005-1016 (2011).
Nep et al., "Grewia Gum 1: Some Mechanical and Swelling Properties of Compact and Film", Trop. J. Pharm. Res., 10 (4): 385-392 (2011).
Patel et al., "Formulation Development and Process Optimization of Theophylline Sustained Release Matrix Tablet", Int. J. of Pharmacy and Pharmaceutical Sciences, 1(2): 31-42 (2009).
Rickard et al., "Hydration Potential of Lysozyme: Protein Dehydration Using a Single Microparticle Technique", Biophysical J., 98: 1075-1084 (2010).
Vlierberghe et al., "Biopolymer-Based Hydrogels As Scaffolds for Tissue Engineering Applications: A Review", Biomacromolecules, 12: 1387-1408 (2011).

* cited by examiner

*Primary Examiner* — Michael B Pallay
(74) *Attorney, Agent, or Firm* — Bibby, McWilliams & Kearney, PLLC; John K. Weatherspoon; Shilpa G. Ghurye

(57) ABSTRACT

A method for manufacturing a drug-delivery composition includes providing at least one pharmaceutically active compound, a dry powder comprising at least a polymer, and an aqueous solution. The dry powder, the pharmaceutically active compound and the aqueous solution are mixed to form a paste-like or semi-solid drug-delivery composition, wherein the aqueous solution is added in an amount of less than or equal to twice the total dry mass of the dry powder.

15 Claims, 7 Drawing Sheets

POLYMERIC DRUG-DELIVERY MATERIAL, METHOD FOR MANUFACTURING THEREOF AND METHOD FOR DELIVERY OF A DRUG-DELIVERY COMPOSITION

FIELD OF THE INVENTION

The present invention belongs to the field of controlled drug release, particularly to methods for manufacturing drug-delivery compositions including pharmaceutically active substances or compounds, and to the controlled delivery thereof into living organisms and tissues for therapeutic purposes.

BACKGROUND OF THE INVENTION

Most therapeutic dosage forms include mixtures of one or more active pharmaceutical ingredients (APIs) with additional components referred to as excipients. APIs are substances which exert a pharmacological effect on a living tissue or organism, whether used for prevention, treatment, or cure of a disease. APIs can occur naturally, be produced synthetically or by recombinant methods, or any combination of these approaches.

Numerous methods have been devised for delivering APIs into living organisms, each with more or less success. Traditional oral therapeutic dosage forms include both solids (tablets, capsules, pills, etc.) and liquids (solutions, suspensions, emulsions, etc.). Parenteral dosage forms include solids and liquids as well as aerosols (administered by inhalers, etc.), injectables (administered with syringes, micro-needle arrays, etc.), topicals (foams, ointments, etc.), and suppositories, among other dosage forms. Although these dosage forms might be effective in delivering low molecular weight APIs, each of these methods suffers from one or more drawbacks, including the lack of bioavailability as well as the inability to completely control either the spatial or the temporal component of the API's distribution when it comes to high molecular weight APIs. These drawbacks are especially challenging for administering biotherapeutics, i.e. pharmaceutically active peptides (e.g. growth factors), proteins (e.g. enzymes, antibodies), oligonucleotides (e.g. RNA, DNA, PNA), hormones and other natural substances or similar synthetic substances, since many of these pharmacologically active biomolecules are at least partially broken down by the digestive tract or in the blood system and are subsequently delivered in suboptimal dosing to the target site.

Therefore, there is an ongoing need for improved drug-delivery methods in life sciences, including but not limited to human and veterinary medicine. One important goal for any new drug-delivery method is to deliver the desired therapeutic agent(s) to a specific place in the body over a specific and controllable period of time, i.e. controlling the delivery of one or more substances to specific organs and tissues in the body with control of the location and release over time. Methods for accomplishing this localized and time controlled delivery are known as controlled-release drug-delivery methods. Delivering APIs to specific organs and tissues in the body offers several potential advantages, including increased patient compliance, extending activity, lowering the required dose, minimizing systemic side effects, and permitting the use of more potent therapeutics. In some cases, controlled-release drug-delivery methods can even allow the administration of therapeutic agents that would otherwise be too toxic or ineffective for use.

There are five broad types of solid dosage forms for controlled-delivery oral administration: reservoir and matrix diffusive dissolution, osmotic, ion-exchange resins, and pro-drugs. For parenterals, most of the above solid dosage forms are available as well as injections (intravenous, intramuscular, etc.), transdermal systems, and implants. Numerous products have been developed for both oral and parenteral administration, including depots, pumps, micro- and nano-particles.

The incorporation of APIs into polymer matrices acting as a core reservoir is one approach for controlling their delivery. Contemporary approaches for formulating such drug-delivery systems are dependent on technological capabilities as well as the specific requirements of the application. For sustained delivery systems there are two main structural approaches: the controlled release by diffusion through a barrier such as shell, coat, or membrane, and the controlled release by the intrinsic local binding strength of the API(s) to the core or to other ingredients in the core reservoir.

Another strategy for controlled delivery of therapeutic agents, especially for delivering biotherapeutics, is their incorporation into polymeric micro- and nano-particles either by covalent or cleavable linkage or by trapping or adsorption inside porous network structures. Various particle architectures can be designed, for instance core/shell structures. Typically one or more APIs are contained either in the core, in the shell, or in both components. Their concentration can vary throughout the respective component in order to modify their release pattern. Although polymeric nanospheres can be effective in the controlled delivery of APIs, they also suffer from several disadvantages. For example, their small size can allow them to diffuse in and out of the target tissue. The use of intravenous nano-particles may also be limited due to rapid clearance by the reticuloendothelial system or macrophages Notwithstanding, polymeric microspheres remain an important delivery vehicle.

In view of the above, there is a need for improving drug-delivery methods and compositions.

SUMMARY OF THE INVENTION

According to an embodiment, a method for manufacturing a drug-delivery composition is provided. The method includes providing at least one pharmaceutically active compound, a dry powder including at least a polymer, and an aqueous solution; and mixing the dry powder, the pharmaceutically active compound and the aqueous solution to form a paste-like or semi-solid drug-delivery composition, wherein the aqueous solution is added in a total amount of less than or equal to twice the total dry mass of the dry powder.

According to an embodiment, a drug-delivery composition is provided, which includes a paste-like or semi-solid mixture including at least a polymer, a pharmaceutically active compound, and an aqueous solution, wherein the total amount of the aqueous solution in the paste-like or semi-solid mixture is less than or equal to twice the total dry mass of the mixture.

According to an embodiment, a method for delivering a drug-delivery composition is provided. The method includes providing a drug-delivery composition including a paste-like or semi-solid mixture having at least a polymer, a pharmaceutically active compound, and an aqueous solution, wherein the total amount of the aqueous solution in the paste-like or semi-solid mixture is less than or equal to twice the total dry mass of the mixture; and applying the drug-delivery composition into a human or animal body.

Those skilled in the art will recognize additional features and advantages upon reading the following detailed description, and upon viewing the accompanying drawings.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated, as they become better understood by reference to the following detailed description. The elements of the drawings are not necessarily to scale relative to each other. Like reference numerals designate corresponding similar parts.

DETAILED DESCRIPTION OF THE INVENTION

Figure 1:
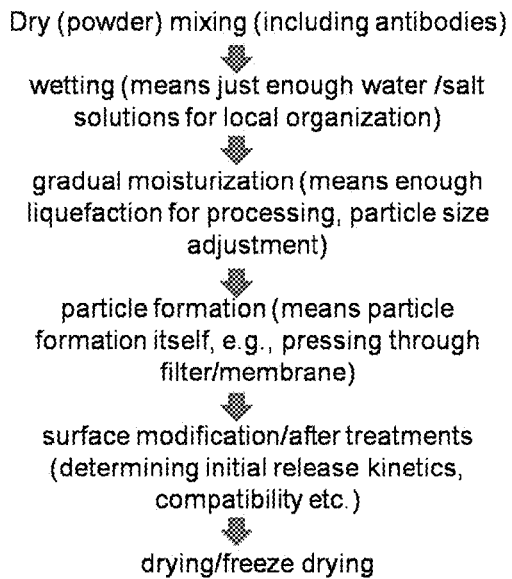
FIG. 1 illustrates processing steps of a manufacturing method according to an embodiment.

The following language and descriptions of certain preferred embodiments of the present invention are provided to further an understanding of the principles of the present invention. However, it will be understood that no limitations of the present invention are intended, and that further alterations, modifications, and applications of the principles of the present invention are also included.

According to an embodiment a drug-delivery composition is manufactured by providing at least one pharmaceutically active compound, a dry powder including at least a polymer, and an aqueous solution. The dry powder, the pharmaceutically active compound and the aqueous solution are then mixed to form a paste-like or semi-solid drug-delivery composition, wherein the aqueous solution is added in an amount less than or equal to twice the total dry mass of the dry powder. The pharmaceutically active compound is referred to hereinafter as active pharmaceutical ingredient (API).

For the purpose of this specification, the term "mixing" intends to describe a mechanical working or a mechanical treatment of the components. For example, mixing can be in the sense of carrying out repeated cycles of pressing and folding or comparable process steps which lead to an intense compression and mixing of the provided water-deficient or quasi-dry compositions and mixtures. Mixing includes, according to an embodiment, pressing and folding of a water-deficient composition including API(s), excipients and an aqueous solution such as water. An embodiment also includes cold extruding of the composition.

The drug-delivery composition includes polymeric delivery materials formed from dry mixtures by a process which can include, according to an embodiment, intimate mixing of a dry powder mixture and then continuously wetting and mixing the powder in a controlled manner, without intermittent drying steps, to achieve an API-containing semi-solid material, possessing superior controlled-delivery properties. It is believed, that the step-wise addition of only small amounts of the aqueous solution such as water, a composite liquid, or a solvent with sustained mixing of the components (e.g. algorithmic pressing-folding cycles) allows for specific molecular interactions by solute shielding layers at interfaces, especially in the vicinity of functional groups and structural elements of the involved macromolecules, which would be otherwise suppressed by self organization or self assembly in free solution or suspension. Such interactions relate to intra-molecular interactions of both excipients and involved APIs but also to intermolecular interactions of both excipients and APIs and of excipients with APIs.

By slowly hydrating and mixing the solid mixture, it is believed that APIs come into better and more-controlled contact with the excipients doing the same with each other. This results in the onset of different interaction mechanisms, which would otherwise not be triggered. The suggested method is especially suitable for formulating biological compounds. Biopolymer-like proteins, peptides, poly- and oligonucleotides are particularly sensitive to changes in their environment and may lose their specific activity more readily than small-molecule APIs. Synthetic APIs and excipients mimicking biomacromolecules may carry both anionic and cationic groups in the relevant medium or may possess different functional groups in variable density on a molecular backbone. These molecules, i.e. biopolymers and polyampholytes are known to have different configurations depending on the molecular environment, i.e. distinct folding patterns, tertiary and quaternary structures. Since a certain activity may be closely related to a certain spatial configuration, these molecules are apt to altered release characteristics when formulated according to the suggested method. Therefore, the approach described herein is believed to have a minimal impact on the natural conformation of the APIs and is thus especially advantageous for the stable formulation of biotherapeutics by controlled release.

The suggested approach combines the benefit of initial thorough dry-mixing with the controlled-release advantages of polymeric micro-spheres but does not suffer from the disadvantages of any of these formulations when applied alone.

The matrix formed by the polymer is typically a hydrophilic matrix but can also include a small amount of hydrophobic substances.

The resulting polymeric drug-delivery materials can be subsequently transferred into the final dosage form either directly or after an optional, later step of forming semi-solid particles, bodies or micro-particles of desired shape, size and size distribution by means of colloid forming techniques and other technological procedures. Remarkably, any solute or dispersant in excess of 200% by weight of the APIs and involved excipients as well as any intermittent drying or evaporating of solute or dispersant from the semi-solid material, may be avoided in order to reach and to maintain the specific properties of the formed API-excipient complex.

According to an embodiment, no additional solute is added during formation of the drug-delivery composition so that the composition does not transform into a more liquid form. According to an embodiment, the drug-delivery composition is not dried but kept as paste. This ensures that the specific release characteristics can be maintained.

The compositions formed by the methods described herein can maintain the drug-releasing properties for a prolonged time such as weeks and months. The APIs remain protected in the paste-like or semi-solid mixture so that their bioavailability can be maintained. If desired, additional barrier layers can be formed around the paste-like or semi-solid mixture.

The suggested method is different from other approaches in that the paste-like or semi-solid composition is formed by addition of a solution to a dry powder of a polymer, which forms the matrix of the composition into which the API is distributed and mixed. According to an embodiment, the paste-like or semi-solid composition is formed by kneading, as an example of algorithmic pressing-folding cycles.

According to an embodiment, the API is provided as dry pharmaceutically active compound powder. The dry polymer powder is homogeneously mixed with the dry pharmaceutically active compound to prepare a dry pre-powder mixture before the aqueous solution is added. The solution can either be added step-wise or continuously. Intensive mechanical working such as kneading may be needed for mixing the dry pre-mixture with the slowly or step-wise added solution to form a paste. It is believed that the intense mechanical interaction with the slow or step-wise addition of the solution results in the specific molecular interaction between the polymer matrix itself and also between the polymer matrix and the API and optional excipients as described above.

According to an embodiment, the added amount of the aqueous solution is less than or equal to twice the total dry mass of the dry powder mixture. According to a further embodiment, the added amount of the aqueous solution is less than or equal to the total dry mass of the dry powder mixture.

The processing can include repeated pressing and folding of the mixture of the dry powder, the pharmaceutically active compound and the aqueous solution to form the paste-like or semi-solid drug-delivery composition. For example, a small amount of the solution is added to the polymer powder or the pre-mixtures of polymer and API. The mechanical processing may start with pressing to bring the mass into a more flat shape and then folding the mass, for example by a blade or other suitable means. The folded mass is then pressed again. By repeating these procedures a distribution of the solution and APIs throughout the powder mass can be achieved. During this mechanical processing, more solution is added so that more and more of the powder mass is "wetted" to form a paste. The addition of the API to the treated system can occur during all phases of the preparation process, and, according to an embodiment, at a late stage after forming an established excipient matrix system. It guarantees a minimum mechanical/mixture influence on the APIs.

According to an embodiment, the mechanical processing of the mass can also include other processes such as rolling.

The force acting on the mass may be limited to avoid excessive mechanical impact that might affect the API. According to an embodiment, a pressure of not more than $10^6$ N·m$^{-2}$ is applied to the mass. According to further embodiments, a pressure of not more than $5 \times 10^5$ N·m$^{-2}$ is applied to the mass.

According to an embodiment, the pharmaceutically active compound (API) is dissolved in the aqueous solution before being mixed with the dry polymer powder. The API is not provided as dry component but as component dissolved in the solution. However, since the solution is added in a limited amount, it is believed that the aforementioned specific molecular interactions also take place.

According to an embodiment, the dry powder and the aqueous solution are mixed to form a paste-like or semi-solid mass and then the pharmaceutically active compound (API) is added to the paste-like or semi-solid mass to form the paste-like or semi-solid drug-delivery composition. The API can either be added in dry or liquid form such as dissolved in a solution. When adding in liquid form, the amount of liquid added should be taken into account for the amount of solution added to the dry powder to keep the drug-delivery composition in paste-like or semi-solid form. The solution added to the dry powder and the solution in which the API is dissolved can be the same or can be different.

According to an embodiment, the API can be provided in particulate form such as micro-particles or nano-particles. Suitable particle size ranges are from about 100 nm to about 50 μm, particularly from about 500 nm to about 30 μm, and more particularly from about 1 μm to about 10 μm.

According to an embodiment, the polymer for the hydrophilic matrix is a hydrophilic polymer that swells when mixed with the aqueous solution. Suitable polymers are polyvinyl alcohol (PVA), polyvinylpyrrolidone (PVP), polyethylene glycol (PEG), gelatin, collagen, alginate, starch, cellulose, chitosan, carboxymethylcellulose, cellulose derivatives, pectin, gum arabic, carrageenan, hyaluronic acid, albumin, fibrin, fibrinogen, synthetic polyelectrolytes, polyethylenimine, acacia gum, xanthan gum, agar agar, polyvinylalcohol, borax, polyacrylic acids including derivatives, protaminsulfate, casein, and derivatives thereof. According to an embodiment, inorganic polymers such as clay and silica can also be used for the hydrophilic matrix. According to an embodiment, the polymer has a molecular weight of at least 10 kDa. Furthermore, polyampholytes can be used as a polymer component. According to an embodiment, a polymer from the group of biopolymers is used. According to an embodiment, a polymer from the group of hydrogel forming substances such as gelatin is used. According to an embodiment, a polymer from the group of polyelectrolyte complex forming substances is used. Such substances typically include two components of opposite charge selected from two polyelectrolytes of opposite charge and a polyelectrolyte and a small ion of opposite charge such as alginate and calcium. According to an embodiment, a polymer from the group of polyampholytes is used. According to an embodiment, a polymer from the group of inorganic gel forming substances is used.

It is assumed that the method as described herein leads to very specific molecular interactions, which define the release characteristics of the polymeric drug-delivery composition. Different to macromolecules in free solution, the amount of the added solution in the method as described herein is so small that the resulting composition cannot be regarded as free solution. Typically, the amount of solution is only equal to, or even only a fraction of, the initial dry powder mass, so that the formulation route is expected to operate along a deficient amount of dissolving water supporting the intimate contact of all possible intermolecular interaction spots. This early, intimate, and controlled contact of the matrix excipients with each other and with APIs establishes various stabilizing and function-improving or -conserving intra- and intermolecular interactions to obtain a more controlled procedure. The method as described herein may employ a ratio of the mass fraction of aqueous solution to the dry matrix components between 0.1 and 2, preferably between 0.3 and 1.2, and most preferably between 0.5 and 1. Consequently, the components cannot be considered to be completely dissolved or dispersed, but should instead be thought of as binding partners for which the other system components compete. Thus, the medium has to be considered as a partner at the same level as the API and the macromolecular excipients. Also, the release medium conditions have to be taken into account in order to obtain a quantitative estimate of the release kinetics. Ultimately, the energy difference with respect to an ideal thermodynamic equilibrium and the presence of activation barriers determine the release conditions of the API from the formulated structure. This is especially relevant because a lower free energy of active binding and lower activation barriers will favor faster release kinetics.

In the novel approach as described herein, the controlled addition of liquid (mainly aqueous solutions or water or composite liquid or solvent) transforms the preparation into a paste- or dough-like consistency, which is appropriate for the production of slow release compositions. The processes according to one embodiment include mixing of all ingredients in dry form in a first step followed by wetting these mixtures and adding liquid media in a controlled manner to transform the wetted mixtures into paste-like or semi-solid consistency. Thus, the interactions of the formulation/fabrication procedures are controlled throughout the method.

As described herein, composite polymeric delivery materials can be formed by maintaining control over strength and sequence of the different API-excipient interactions from the beginning of the process. Thus, even during the initial dry-powder mixing, the interactions occur under essentially non-wetted conditions. These interactions are switched on or off or modified by the step-wise addition of limited amounts of liquid media such as water, protic solvents (e.g. acetic acid) or aqueous solutions. This approach also helps to minimize the use of excipients and water or solvent, since these formulation routes are processed under minimal water/solvent conditions. Thus, one aspect of the method described herein is the ability to start with maximum concentration of the API(s). For example, a gelatin gel is stabilized by more or less hydrophobic spots distributed at a given concentration throughout the self-organized gel. The spot concentration depends on the dissolved gelatin concentration. The proposed novel approach increases the gelatin stabilizing hydrophobic spot concentration or equivalently the material concentration per spot far above this equilibrium value by the addition of both, low amounts of water and mechanical treatment overcoming the repulsive barriers for forming the high concentration stabilizing spots throughout the gel/water mass. Surprisingly, this new configuration demonstrates a tremendous stability (meta-stability) created by a driven process as opposed to self-organization or self-assembly.

Independent of the selected route, the precise control of all interactions between the APIs and excipients is desired in order to achieve successful formulation, even if excipients form membranes that have to be penetrated by the APIs. Thus, the methods as described herein starts with maximum concentrations of both the APIs and the excipients according to an embodiment and subsequently adapt the conditions during the process of mixture, structuring, manufacturing, and polymeric delivery material formation up to the essential concentrations in the final delivery forms.

According to an embodiment, APIs can be small molecules, peptides, proteins, therapeutic proteins, antibodies, antigens, enzymes, receptor ligands, nucleotides or nucleotide analogs, oligonucleotides and oligonucleotide analogs, genes or gene-like species, viruses, virus-like particles, sugars or polysaccharides or their analogs, or any other physical composition such as living organelles, cells, or tissue constituents. According to an embodiment. Excipients can include almost any member of these same classes of species. They often act as buffer, filler, binder, osmotic agent, lubricant, or fulfill similar functions. Polyampholytes are multiply-charged polymers which bear both anionic and cationic groups in the relevant medium, e.g. in an aqueous solution. The various classes and types of APIs, excipients, polymers, and polyampholytes are familiar to those skilled in the art of drug delivery.

According to an embodiment, the excipient can be, for example, a sugar such as monosaccharides, disaccharides, oligosaccharides, polysaccharides, or albumin, chitosan, collagen, collagen-n-hydroxysuccinimide, fibrin, fibrinogen, gelatin, globulin, polyaminoacids, polyurethane comprising amino acids, prolamin, protein-based polymers, copolymers and derivatives thereof, and mixtures thereof.

According to an embodiment, the pharmaceutically active compound can be one or more of immunoglobulins, fragments or fractions of immunoglobulins, synthetic substance mimicking immunoglobulins or synthetic, semisynthetic or biosynthetic fragments or fractions thereof, chimeric, humanized or human monoclonal antibodies, Fab fragments, fusion proteins or receptor antagonists (e.g., anti-TNF alpha, Interleukin-1, Interleukin-6 etc.), antiangiogenic compounds (e.g., anti-VEGF, anti-PDGF etc.), intracellular signaling inhibitors (e.g JAK1,3 and SYK inhibitors), peptides having a molecular mass equal to or higher than 3 kDa, ribonucleic acids (RNA), desoxyribonucleic acids (DNA), plasmids, peptide nucleic acids (PNA), steroids, corticosteroids, an adrenocorticostatic, an antibiotic, an antidepressant, an antimycotic, a [beta]-adrenolytic, an androgen or antiandrogen, an antianemic, an anabolic, an anaesthetic, an analeptic, an antiallergic, an antiarrhythmic, an antiarterosclerotic, an antibiotic, an antifibrinolytic, an anticonvulsive, an antiinflammatory drug, an anticholinergic, an antihistaminic, an antihypertensive, an antihypotensive, an anticoagulant, an antiseptic, an antihemorrhagic, an antimyasthenic, an antiphlogistic, an antipyretic, a beta-receptor antagonist, a calcium channel antagonist, a cell, a cell differentiation factor, a chemokine, a chemotherapeutic, a coenzyme, a cytotoxic agent, a prodrug of a cytotoxic agent, a cytostatic, an enzyme and its synthetic or biosynthetic analogue, a glucocorticoid, a growth factor, a haemostatic, a hormone and its synthetic or biosynthetic analogue, an immunosuppressant, an immunostimulant, a mitogen, a physiological or pharmacological inhibitor of mitogens, a mineralcorticoid, a muscle relaxant, a narcotic, a neurotransmitter, a precursor of a neurotransmitter, an oligonucleotide, a peptide, a (para)-sympathicomimetic, a (para)-sympatholytic, a protein, a sedating agent, a spasmolytic, a vasoconstrictor, a vasodilatator, a vector, a virus, a virus-like particle, a virustatic, a wound-healing substance, and combinations thereof.

According to an embodiment, the drug-delivery composition can be brought into an implantable form to form an implantable drug-delivery formulation with controlled-release kinetics. The bringing into an implantable form can include addition of biodegradable or bioerodible polymers. The polymer matrix itself according to the novel proposed approach can also be comprised of biodegradable or bioerodible polymers. Furthermore, a micro-porous membrane made from ethylene/vinyl acetate copolymer or other materials for ocular use can be formed around the paste-like or semi-solid mixture. Further options include use of biodegradable polymers for subcutaneous and intramuscular injection, bioerodible polysaccharides, hydrogels. The implantable drug-delivery formulation can be activated by osmotic pressure, or any other mechanism tested in the past, like vapor pressure or magnetism.

The approach described herein distinguishes from oral formulations such as tablets, caplets, and pills in that a paste-like or semi-solid composition is prepared. Commonly known administered formulations may include powder mixtures. However, they are merely compressed or coated compacts produced from thoroughly mixed amorphous or crystalline powders.

The present invention encompasses not only the use of pure aqueous media but can comprise also minor amounts of plant oils or any other pharmaceutically acceptable solvents or their mixtures. The method and composition described herein can use any substance which can exert a therapeutic effect, including small molecules, synthetic or biological macromolecules such as peptides, proteins, oligonucleotides, carbohydrates, and others familiar to one skilled in the art.

The polymeric delivery materials of the present invention can optionally be labeled with any of a wide variety of agents, which are known to those skilled in the art. As examples, dyes, fluorophores, chemiluminescent agents, isotopes, metal atoms or clusters, radionuclides, enzymes, antibodies, or tight-binding partners such as biotin and avidin can all be used to label the polymeric drug-delivery composition for detection, localization, imaging, or any other analytical or medical purpose. The polymeric delivery composition, particularly the polymer of the matrix, can also optionally be coated or conjugated with a wide variety of molecules in order to modify its function, improve its stability, or further modify the rate of release of the API. As examples, the drug-delivery composition can be coated with a covalently- or non-covalently-attached layer of a species such as small molecules, hormones, peptides, proteins, phospholipids, polysaccharides, mucins, or biocompatible polymers such polyethylene glycol (PEG), dextran, or any of a number of comparable materials. The wide range of materials, which can be used in this fashion, and the methods for accomplishing these processes, are well known to those skilled in the art.

It will also be apparent to one skilled in the art that the various starting components such as the polymer powder and the API can be further manipulated and processed using a wide variety of methods, processes, and equipment familiar to one skilled in the art. For example, the dry components can be thoroughly mixed using any of a number of known methods and equipments, such as trituration with a mortar and pestle or blending in a Patterson-Kelley twin-shell blender, before the initiation of the wetting stage. Further a wide variety of shapes, sizes, morphologies, and surface compositions of the drug-delivery composition can be formed. For example, micro-particles or cylindrical bodies with different aspect ratios can be prepared by means of mechanical milling, molding, extruding or similar processes of the paste-like or semi-solid or even solid wet polymeric material. The resulting particles can be further treated to prepare them for specific applications such as e.g. drug delivery systems. As another example, the polymeric particles and bodies can be immersed into oil such as plant oil for conservation and storage. As yet another example, transforming the wetted mixture, paste or dough into micro-particles or polymeric bodies by means of processes such as drying, rheological methods, grinding, milling, pressure homogenization, molding, and/or other such well-established procedures can yield a wide range of final products. As another example, the polymeric drug-delivery composition can be squeezed through a sieving disk containing predefined pores or channels with uniform pore geometry and diameter by an extrusion process, e.g. in a repeating manner.

According to an embodiment, the paste-like or semi-solid mixture drug-delivery composition has a modulus of elasticity of at least $10^{-4}$ N·mm$^{-2}$. According to an embodiment, the paste-like or semi-solid mixture drug-delivery composition has a modulus of elasticity of at least $10^{-3}$ N·mm$^{-2}$, and particularly $10^{-2}$ N·mm$^{-2}$, and more particularly $10^{-1}$ N·mm$^{-2}$.

According to an embodiment, the paste-like or semi-solid mixture has a viscosity of not more than 500 Pa·s, and particularly of not more than 300 Pa·s. According to an embodiment, the paste-like or semi-solid mixtures has a viscosity of not less than few mPa·s, for example 100 mPa·s, and particularly of not less than 1 Pa·s.

According to an embodiment, the pharmaceutical active compound is provided as powder containing particles ranging from about 100 nm to about 50 μm, particularly from about 500 nm to about 30 μm, and more particularly from about 1 μm to about 10 μm.

FIG. 1 illustrates processing steps of a manufacturing method according to an embodiment. An aspect of this embodiment is that the overall amount of water added is deficient with respect to dissolution of the excipients. First, the dry polymer powder is mixed together with the API, for example, antibodies. In a further process, this dry mixture is gradually wetted and mechanically worked to obtain a paste. It should be noted that the aqueous solution is gradually added to the dry mixture different to other approaches, which gradually add a dry powder to a solution. In further processes, the paste can be further processed to obtain particles of a given size, shape and size distribution. In further processes, the thus formed particles can be dried, for example by freeze-drying.

Figure 2:
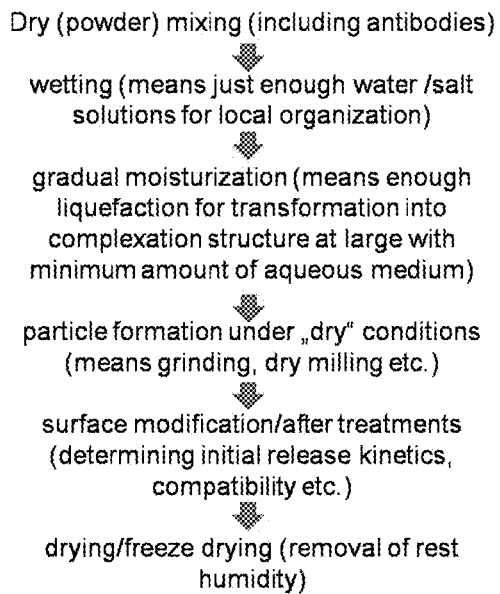
FIG. 2 illustrates processing steps of a manufacturing method according to an embodiment.

FIG. 2 illustrates processing steps of a manufacturing method according to an embodiment. The aspect of this embodiment is that the overall amount of water added is deficient with respect to dissolution of the excipients. The particle formation via quasi-dry conditions in grinding and milling processes are embodiments of the mechanical procedures such as algorithmic cycles of pressing and folding/mixing.

Similar to the embodiment of FIG. 1, a dry powder is prepared by mixing with a subsequent wetting of the same. In further processes, mechanical working such as grinding or milling is used to form particles from the wetted composition, which exhibit solid-like properties. In further processes, the surface of the particles is modified to further alter the release characteristics. In further processes, the solution added to the mixture is removed.

In the following, specific examples are described.

Example 1

Figure 3:
FIG. 3 shows a photograph of the stable gelatin body obtained according to an embodiment and according to the procedure of FIG. 2.

Dry gelatin (10 g) is mixed with small aliquots (1 g) of water in a series of consecutive steps under steady kneading up to a gelatin-to-water ratio of 2. Continuous kneading/mixing for 3 minutes leads to a single gelatin body of well-defined elasticity but only small plasticity. The introduction of this gelatin body into water at room temperature results in a stable, gelatinous body, which does not swell significantly over a period of days and weeks (cp. FIG. 3).

Example 2

Figure 4A:
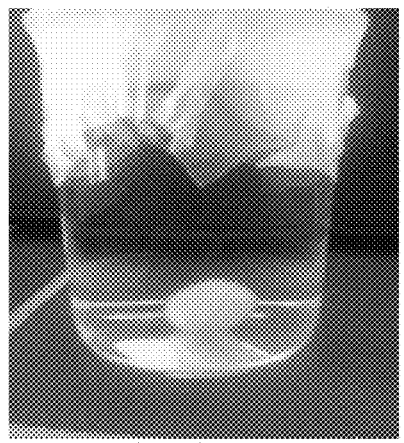
FIGS. 4a and 4b show photographs of water-based formulations of gelatin-water mixtures according to the procedure illustrated in FIG. 2 and described by the experiment of FIG. 3.
Figure 4B:
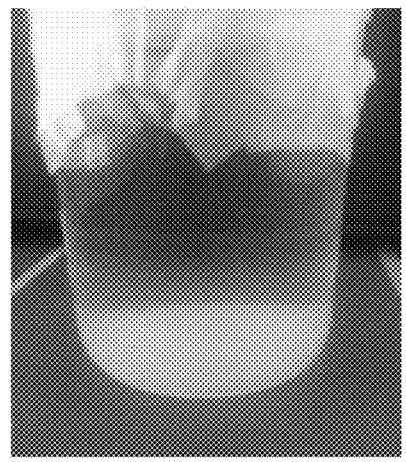
Figure 5A:
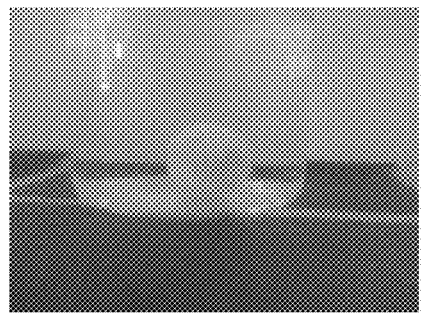
FIG. 5 demonstrates a series of eight photographs of dry-route formulations (prepared as described in FIG. 2) combining carboxymethylcellulose (CMC) with chitosan.
Figure 5B:
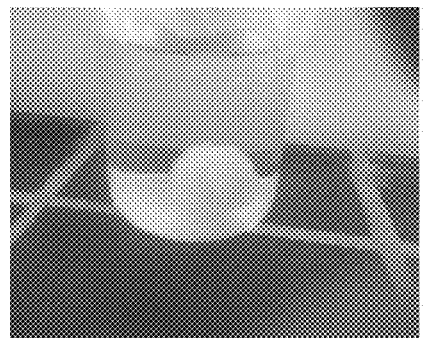
Figure 5C:
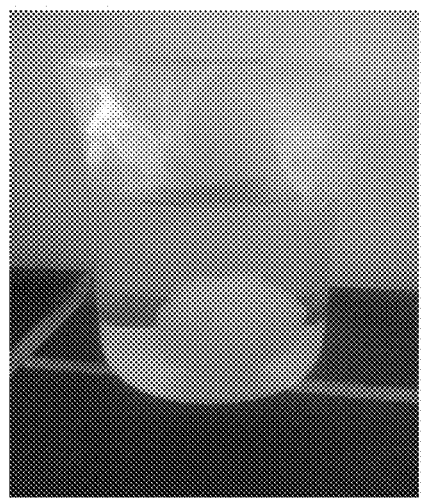
Figure 5D:
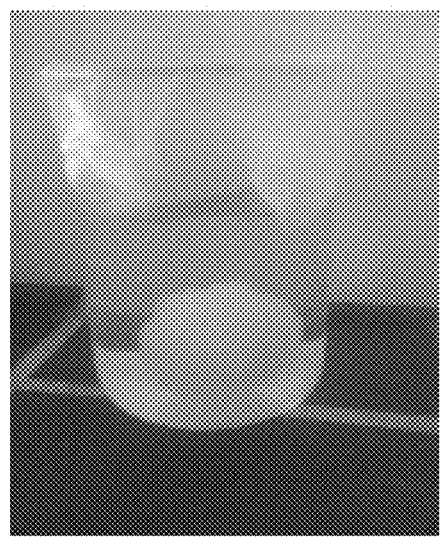
Figure 5E:
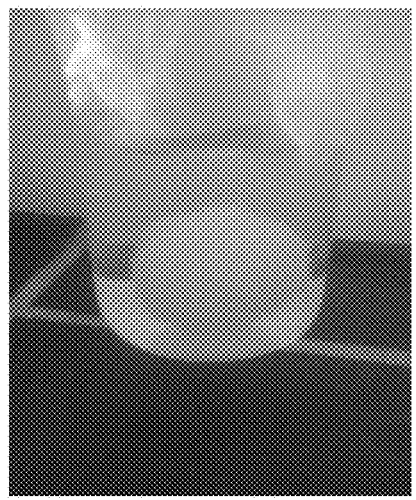
Figure 5F:
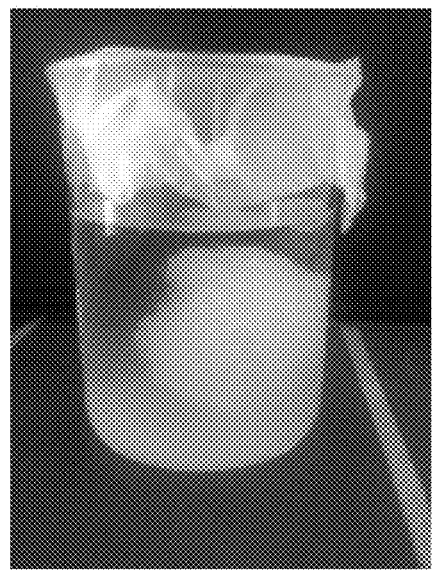
Figure 5G:
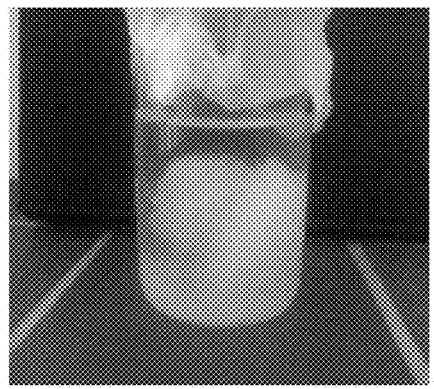
Figure 5H:

Dry gelatin (10 g) is mixed with 5 g of water. In contrast to the preparation process of FIG. 3 the mechanical kneading was carried out for a time period of 10 seconds only. The obtained gelatin body is presented in FIG. 4a right after formulation. The total disintegration of the gelatin body ten hours after formulation is given in FIG. 4b. The water of the beaker is starting to gel and forms a continuous gelatinous body about 30 hours after formulation.

Example 3

5 ml of water was added to a mixture of 5 g of carboxymethylcellulose and 5 g of chitosan. This mixture was mechanically kneaded for 3 minutes and the solid body demonstrated in FIG. 5 (a) was formed and suspended in water at room temperature. This same system was photographed after predefined periods of time as presented in FIG. 5 (b) to (h). A continuous swelling process is observed during the first documentation period of 42 hours, however, not leading to disintegration of the solid mass. Disintegration was observed with a 10 second treatment of the same composition (not shown) as observed in the gelatin system of Example 2 (FIG. 4). Further observation of the mechanically treated composition up to 145 hours after preparation demonstrates an increasing tendency of disintegration. The stabilization effect via the mechanical treatment is clearly visible during the first 42 hours; however, it is much less expressed as compared to the gelatin composition as presented in FIG. 3.

Example 4

Figure 6A:
FIG. 6 presents a series of six photographs of dry-route formulations according to FIG. 2 combining carboxymethylcellulose with chitosan beginning with (a) acetic acid and (b) plant oil as wetting agents.
Figure 6B:
Figure 6C:
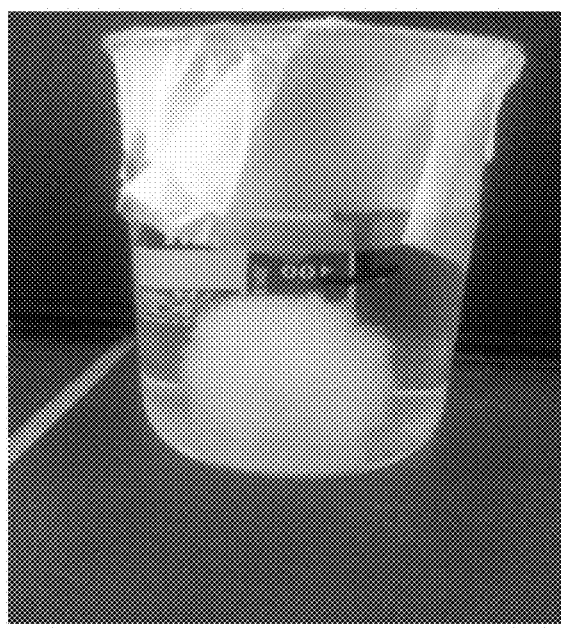

Equal amounts of dry carboxymethylcellulose and dry chitosan (5 g each) are mixed with 5 g of acetic acid (pH 3) and a small amount (less than 1 g) of plant oil. The mixture is mechanically treated for 3 minutes and formed into a spherical body. It is suspended into water at room temperature (FIG. 6a) and observed over time (FIG. 6b, after 4 hours). Despite a clearly visible swelling there is no disintegration during the 27 hours observation period (FIG. 6c). The CMC/chitosan system is much less stable than the gelatin system (EXAMPLE 1). If the system is mechanically treated for only 10 seconds the disintegration of the spherical body after suspension into water at room temperature is starting more or less directly (not shown) and its behavior is, at least in principle, comparable to the gelatin system of EXAMPLE 2. The gelatin system shows a little more stability.

Example 5

Figure 7:
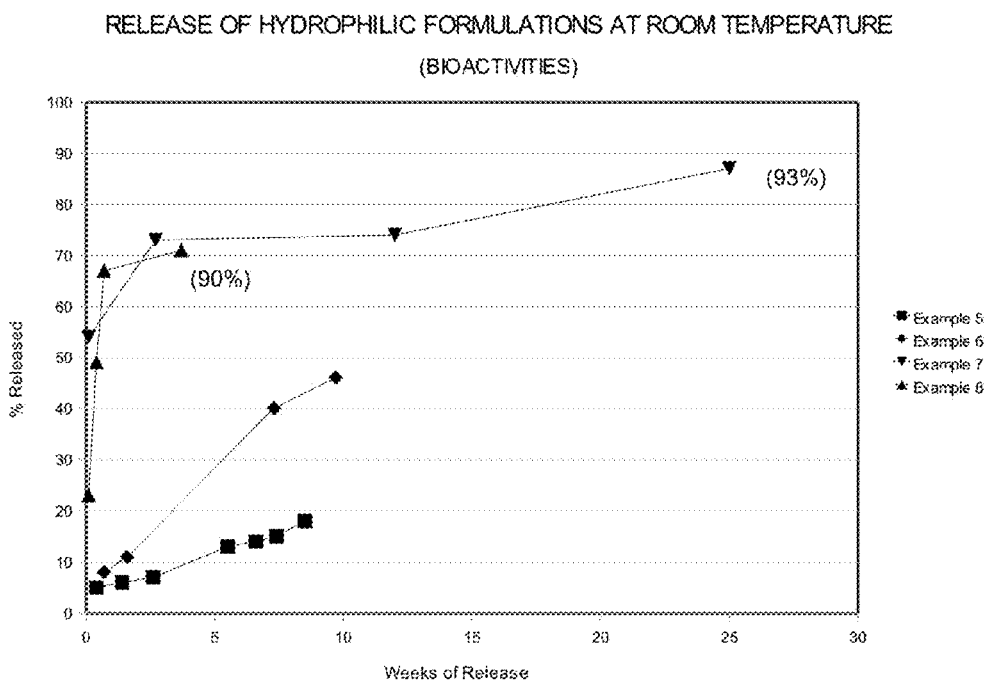
FIG. 7 presents antibody release curves from drug-delivery compositions prepared according to several examples illustrating embodiments.

First, a calcium alginate film was prepared by addition of a calcium chloride solution to 1.0 g aqueous alginate gel (2%, 0.01% sodium azide) in a flat bowl. After 10 minutes the resulting film was separated from mold and dried for 2 minutes on white filter paper. Second, 2 mg of antibody 1 of the type of gamma globulin was placed onto the centre of the film. Third, the film was folded together and kneaded by hand for 7 minutes forming ultimately a spherical particle. To this particle, 1.0 g of an isotonic sodium chloride solution was added. The release of antibody 1 was determined spectroscopically by the UV 280 nm method under sink conditions (cp. FIG. 7, Example 5). Ultimately we observed a very slow release rate (18.5% after 8.5 weeks).

Example 6

First, a calcium alginate film was prepared by addition of a calcium chloride solution to 1.0 g aqueous alginate gel (2%, 0.01% sodium azide) in a flat bowl. After 10 minutes the resulting film was separated from the mold and dried for 2 minutes on white filter paper. Second, 25 mg of microcrystalline cellulose and 50 mg of an aqueous antibody 2 (of the gamma globulin type) solution was placed onto the center of the film. Third, the film was folded together and kneaded by hand for 7 minutes forming ultimately a spherical particle. To this particle 1.2 g of an isotonic sodium chloride solution was added. The release of antibody 2 was determined spectroscopically by the UV 280 nm method under sink conditions (cp. FIG. 7, Example 6). Ultimately we observed a medium release rate of 46% in 9.7 weeks. After 3.7 weeks about 90% of released antibody 2 is active.

Example 7

66 mg of an antibody 2 solution (25 mg/ml) was added to 24 mg of micro-crystalline cellulose and 90 mg of castor oil. This mixture was mechanically treated using a glass rod for 1 minute. The resulting product was mixed with 1.5 g of an aqueous alginate gel (2%, 0.01% sodium azide) and then dropped into a cold aqueous calcium chloride solution (18%) under stirring (magnetic stirrer 500 U/min). The obtained capsules were separated from suspension and washed two times with double distilled water. The resulting alginate capsules were added to 3.0 g of an isotonic sodium chloride solution (0.01% azide). The release of antibody 2 was determined spectroscopically by the UV 280 nm method under no-sink conditions (cp. FIG. 7, Example 7). This system represents a mixed hydrophilic/hydrophobic system. The resulting release behavior is demonstrating a two-phase characteristic; after a fast release period of 73% in 2.7 weeks there is a slowing down to another 14% over the next 22 weeks. After 25 weeks of release about 93% or the released antibody 2 is bio-active as checked by ELISA.

Example 8

200 mg of an antibody 3 (of gamma globulin type) solution (50 mg/ml) was added to 80 mg micro-crystalline cellulose and 90 mg of castor oil. This mixture was mechanically treated using a glass rod for 1 minute. The resulting product was mixed with 1.0 g of an aqueous alginate gel (2%) and then dropped into a cold aqueous calcium chloride solution (18%) under stirring (magnetic stirrer 500 U/min). The obtained capsules were separated from suspension and washed two times with double distilled water and finally added to 5.0 g of an isotonic sodium chloride solution. The release of antibody 3 was determined spectroscopically by the UV 280 nm method under no-sink conditions (cp. FIG. 7, Example 8). Ultimately, we observed a similar behavior as in previous EXAMPLE 7. After about 4 weeks of release about 90% of the released antibody 3 is bio-active as determined by ELISA.

The invention claimed is:
1. A method for manufacturing a controlled-release drug-delivery composition, consisting of:
   a first mixing step of mixing a dry powder consisting of a polymer; and a second mixing step of mixing the dry powder with an aqueous solution consisting of a pharmaceutically active compound to form a paste or semi-solid material;

wherein the aqueous solution is gradually added to the dry powder in a total amount less than, equal to or equal to twice the total dry mass of the dry powder, wherein the ratio of the mass fraction of the aqueous solution to the dry powder is between 0.5 and 1, wherein at least a portion of the aqueous solution added in the second mixing step is gradually added during mechanical kneading.

2. The method of claim 1, wherein the pharmaceutically active compound is selected from the group consisting of immunoglobulins, fragments or fractions of immunoglobulins, synthetic substance mimicking immunoglobulins or synthetic, semisynthetic or biosynthetic fragments or fractions thereof, chimeric, humanized or human monoclonal antibodies, Fab fragments, fusion proteins or receptor antagonists, antiangiogenic compounds, intracellular signaling inhibitors, peptides having a molecular mass equal to or higher than 3 kDa, ribonucleic acids (RNA), desoxyribonucleic acids (DNA), plasmids, peptide nucleic acids (PNA), steroids, corticosteroids, an adrenocorticostatic, an antibiotic, an antidepressant, an antimycotic, a beta-adrenolytic, an androgen or antiandrogen, an antianemic, an anabolic, an anaesthetic, an analeptic, an antiallergic, an antiarrhythmic, an antiarterosclerotic, an antibiotic, an antifibrinolytic, an anticonvulsive, an antiinflammatory drug, an anticholinergic, an antihistaminic, an antihypertensive, an antihypotensive, an anticoagulant, an antiseptic, an antihemorrhagic, an antimyasthenic, an antiphlogistic, an antipyretic, a beta-receptor antagonist, a calcium channel antagonist, a cell, a cell differentiation factor, a chemokine, a chemotherapeutic, a coenzyme, a cytotoxic agent, a prodrug of a cytotoxic agent, a cytostatic, an enzyme and its synthetic or biosynthetic analogue, a glucocorticoid, a growth factor, a haemostatic, a hormone and its synthetic or biosynthetic analogue, an immunosuppressant, an immunostimulant, a mitogen, a physiological or pharmacological inhibitor of mitogens, a mineralcorticoid, a muscle relaxant, a narcotic, a neurotransmitter, a precursor of a neurotransmitter, an oligonucleotide, a peptide, a para-sympathicomimetic, a para-sympatholytic, a protein, a sedating agent, a spasmolytic, a vasoconstrictor, a vasodilatator, a vector, a virus, a viral particle, a virustatic, a wound-healing substance, and combinations thereof.

3. The method of claim 1, wherein the pharmaceutically active compound is an antibody.

4. The method of claim 1, wherein the polymer is selected from the group consisting of polyvinyl alcohol (PVA), polyvinylpyrrolidone (PVP), polyethylene glycol (PEG), gelatin, collagen, alginate, starch, cellulose, chitosan, carboxymethylcellulose, cellulose derivatives, pectin, gum arabic, carrageenan, hyaluronic acid, albumin, fibrin, fibrinogen, synthetic polyelectrolytes, polyethylenimine, acacia gum, xanthan gum, agar agar, polyvinylalcohol, borax, polyacrylic acids, protaminsulfate, and casein.

5. A method for manufacturing a controlled-release drug-delivery composition, consisting of:

a first mixing step of mixing a dry powder consisting of a polymer and a pharmaceutically active compound; and a second mixing step of mixing the dry powder with an aqueous solution to form a paste or semi-solid material;

wherein the aqueous solution is gradually added to the dry powder in a total amount less than, equal to or equal to twice the total dry mass of the dry powder, wherein the ratio of the mass fraction of the aqueous solution to the dry powder is between 0.5 and 1, wherein at least a portion of the aqueous solution added in the second mixing step is gradually added to the dry powder during mechanical kneading.

6. The method of claim 5, wherein the pharmaceutically active compound is selected from the group consisting of immunoglobulins, fragments or fractions of immunoglobulins, synthetic substance mimicking immunoglobulins or synthetic, semisynthetic or biosynthetic fragments or fractions thereof, chimeric, humanized or human monoclonal antibodies, Fab fragments, fusion proteins or receptor antagonists, antiangiogenic compounds, intracellular signaling inhibitors, peptides having a molecular mass equal to or higher than 3 kDa, ribonucleic acids (RNA), desoxyribonucleic acids (DNA), plasmids, peptide nucleic acids (PNA), steroids, corticosteroids, an adrenocorticostatic, an antibiotic, an antidepressant, an antimycotic, a beta-adrenolytic, an androgen or antiandrogen, an antianemic, an anabolic, an anaesthetic, an analeptic, an antiallergic, an antiarrhythmic, an antiarterosclerotic, an antibiotic, an antifibrinolytic, an anticonvulsive, an antiinflammatory drug, an anticholinergic, an antihistaminic, an antihypertensive, an antihypotensive, an anticoagulant, an antiseptic, an antihemorrhagic, an antimyasthenic, an antiphlogistic, an antipyretic, a beta-receptor antagonist, a calcium channel antagonist, a cell, a cell differentiation factor, a chemokine, a chemotherapeutic, a coenzyme, a cytotoxic agent, a prodrug of a cytotoxic agent, a cytostatic, an enzyme and its synthetic or biosynthetic analogue, a glucocorticoid, a growth factor, a haemostatic, a hormone and its synthetic or biosynthetic analogue, an immunosuppressant, an immunostimulant, a mitogen, a physiological or pharmacological inhibitor of mitogens, a mineralcorticoid, a muscle relaxant, a narcotic, a neurotransmitter, a precursor of a neurotransmitter, an oligonucleotide, a peptide, a para-sympathicomimetic, a para-sympatholytic, a protein, a sedating agent, a spasmolytic, a vasoconstrictor, a vasodilatator, a vector, a virus, a viral particle, a virustatic, a wound-healing substance, and combinations thereof.

7. The method of claim 5, wherein the pharmaceutically active compound is an antibody.

8. The method of claim 5, wherein the polymer is selected from the group consisting of polyvinyl alcohol (PVA), polyvinylpyrrolidone (PVP), polyethylene glycol (PEG), gelatin, collagen, alginate, starch, cellulose, chitosan, carboxymethylcellulose, cellulose derivatives, pectin, gum arabic, carrageenan, hyaluronic acid, albumin, fibrin, fibrinogen, synthetic polyelectrolytes, polyethylenimine, acacia gum, xanthan gum, agar agar, polyvinylalcohol, borax, polyacrylic acids, protaminsulfate, and casein.

9. A method for manufacturing a controlled-release drug-delivery composition, consisting of:

a first mixing step of mixing a dry powder consisting of a polymer;

a second mixing step of mixing the dry powder with an aqueous solution to form a paste or material;

wherein the aqueous solution is gradually added to the dry powder in a total amount less than, equal to or equal to twice the total dry mass of the dry powder, wherein the ratio of the mass fraction of the aqueous solution to the dry powder is between 0.5 and 1;

wherein at least a portion of the aqueous solution added in the second mixing step is gradually added to the dry powder during mechanical kneading; and a third mixing step of mixing a pharmaceutically active compound with the paste or semi-solid material to form a paste drug-delivery composition or semi-solid drug-delivery composition;

wherein the third mixing step consists of mechanical kneading.

10. The method of claim 9, wherein the pharmaceutically active compound is selected from the group consisting of immunoglobulins, fragments or fractions of immunoglobulins, synthetic substance mimicking immunoglobulins or synthetic, semisynthetic or biosynthetic fragments or fractions thereof, chimeric, humanized or human monoclonal antibodies, Fab fragments, fusion proteins or receptor antagonists, antiangiogenic compound, intracellular signaling inhibitors, peptides having a molecular mass equal to or higher than 3 kDa, ribonucleic acids (RNA), desoxyribonucleic acids (DNA), plasmids, peptide nucleic acids (PNA), steroids, corticosteroids, an adrenocorticostatic, an antibiotic, an antidepressant, an antimycotic, a beta-adrenolytic, an androgen or antiandrogen, an antianemic, an anabolic, an anaesthetic, an analeptic, an antiallergic, an antiarrhythmic, an antiarterosclerotic, an antibiotic, an antifibrinolytic, an anticonvulsive, an antiinflammatory drug, an anticholinergic, an antihistaminic, an antihypertensive, an antihypotensive, an anticoagulant, an antiseptic, an antihemorrhagic, an antimyasthenic, an antiphlogistic, an antipyretic, a beta-receptor antagonist, a calcium channel antagonist, a cell, a cell differentiation factor, a chemokine, a chemotherapeutic, a coenzyme, a cytotoxic agent, a prodrug of a cytotoxic agent, a cytostatic, an enzyme and its synthetic or biosynthetic analogue, a glucocorticoid, a growth factor, a haemostatic, a hormone and its synthetic or biosynthetic analogue, an immunosuppressant, an immunostimulant, a mitogen, a physiological or pharmacological inhibitor of mitogens, a mineralcorticoid, a muscle relaxant, a narcotic, a neurotransmitter, a precursor of a neurotransmitter, an oligonucleotide, a peptide, a para-sympathicomimetic, a para-sympatholytic, a protein, a sedating agent, a spasmolytic, a vasoconstrictor, a vasodilatator, a vector, a virus, a viral particle, a virustatic, a wound-healing substance, and combinations thereof.

11. The method of claim 9, wherein the pharmaceutically active compound is an antibody.

12. The method of claim 9, wherein the polymer is selected from the group consisting of polyvinyl alcohol (PVA), polyvinylpyrrolidone (PVP), polyethylene glycol (PEG), gelatin, collagen, alginate, starch, cellulose, chitosan, carboxymethylcellulose, cellulose derivatives, pectin, gum arabic, carrageenan, hyaluronic acid, albumin, fibrin, fibrinogen, synthetic polyelectrolytes, polyethylenimine, acacia gum, xanthan gum, agar agar, polyvinylalcohol, borax, polyacrylic acids, protaminsulfate, and casein.

13. A method for manufacturing a controlled-release drug-delivery composition, consisting of:

a first mixing step of mixing a dry powder consisting of a polymer, wherein the polymer is selected from the group consisting of polyvinyl alcohol (PVA), polyvinylpyrrolidone (PVP), polyethylene glycol (PEG), gelatin, collagen, alginate, starch, cellulose, chitosan, carboxymethylcellulose, cellulose derivatives, pectin, gum arabic, carrageenan, hyaluronic acid, albumin, fibrin, fibrinogen, synthetic polyelectrolytes, polyethylenimine, acacia gum, xanthan gum, agar agar, polyvinylalcohol, borax, polyacrylic acids, protaminsulfate, and casein; and a second mixing step of mixing the dry powder with an aqueous solution consisting of a pharmaceutically active compound to form a paste or semi-solid material, wherein the pharmaceutically active compound is selected from the group consisting of antibody, immunoglobulins, fragments or fractions of immunoglobulins, synthetic substance mimicking immunoglobulins or synthetic, semisynthetic or biosynthetic fragments or fractions thereof, chimeric, humanized or human monoclonal antibodies, Fab fragments, fusion proteins or receptor antagonists, antiangiogenic compounds, intracellular signaling inhibitors, peptides having a molecular mass equal to or higher than 3 kDa, ribonucleic acids (RNA), desoxyribonucleic acids (DNA), plasmids, peptide nucleic acids (PNA), steroids, corticosteroids, an adrenocorticostatic, an antibiotic, an antidepressant, an antimycotic, a beta-adrenolytic, an androgen or antiandrogen, an antianemic, an anabolic, an anaesthetic, an analeptic, an antiallergic, an antiarrhythmic, an antiarterosclerotic, an antibiotic, an antifibrinolytic, an anticonvulsive, an antiinflammatory drug, an anticholinergic, an antihistaminic, an antihypertensive, an antihypotensive, an anticoagulant, an antiseptic, an antihemorrhagic, an antimyasthenic, an antiphlogistic, an antipyretic, a beta-receptor antagonist, a calcium channel antagonist, a cell, a cell differentiation factor, a chemokine, a chemotherapeutic, a coenzyme, a cytotoxic agent, a prodrug of a cytotoxic agent, a cytostatic, an enzyme and its synthetic or biosynthetic analogue, a glucocorticoid, a growth factor, a haemostatic, a hormone and its synthetic or biosynthetic analogue, an immunosuppressant, an immunostimulant, a mitogen, a physiological or pharmacological inhibitor of mitogens, a mineralcorticoid, a muscle relaxant, a narcotic, a neurotransmitter, a precursor of a neurotransmitter, an oligonucleotide, a peptide, a para-sympathicomimetic, a para-sympatholytic, a protein, a sedating agent, a spasmolytic, a vasoconstrictor, a vasodilatator, a vector, a virus, a viral particle, a virustatic, a wound-healing substance, and combinations thereof;

wherein the aqueous solution is gradually added to the dry powder in a total amount less than, equal to or equal to twice or in an amount at most equal to the total dry mass of the dry powder, wherein the ratio of the mass fraction of the aqueous solution to the dry powder is between 0.5 and 1, wherein at least a portion of the aqueous solution added in the second mixing step is gradually added during mechanical kneading.

14. A method for manufacturing a controlled-release drug-delivery composition, consisting of:

a first mixing step of mixing a dry powder consisting of a polymer and a pharmaceutically active compound, wherein the polymer is selected from the group consisting of polyvinyl alcohol (PVA), polyvinylpyrrolidone (PVP), polyethylene glycol (PEG), gelatin, collagen, alginate, starch, cellulose, chitosan, carboxymethylcellulose, cellulose derivatives, pectin, gum arabic, carrageenan, hyaluronic acid, albumin, fibrin, fibrinogen, synthetic polyelectrolytes, polyethylenimine, acacia gum, xanthan gum, agar agar, polyvinylalcohol, borax, polyacrylic acids, protaminsulfate, and casein, wherein the pharmaceutically active compound is selected from the group consisting of antibody, immunoglobulins, fragments or fractions of immunoglobulins, synthetic substance mimicking immunoglobulins or synthetic, semisynthetic or biosynthetic fragments or fractions thereof, chimeric, humanized or human monoclonal antibodies, Fab fragments, fusion proteins or receptor antagonists, antiangiogenic compounds, intracellular signaling inhibitors, peptides having a molecular mass equal to or higher than 3 kDa, ribonucleic acids (RNA), desoxyribonucleic acids (DNA), plasmids, peptide nucleic acids (PNA), steroids, corticosteroids, an adrenocorticostatic, an antibiotic, an antidepressant, an antimycotic, a beta-adrenolytic, an androgen or antiandrogen, an antianemic, an anabolic, an anaesthetic, an analeptic, an antiallergic, an antiarrhythmic, an antiarterosclerotic, an antibiotic, an antifibrinolytic, an anticonvulsive, an antiinflammatory drug, an anticholinergic, an antihistaminic, an antihypertensive, an antihypotensive, an anticoagulant, an antiseptic, an antihemorrhagic, an antimyasthenic, an antiphlogistic, an antipyretic, a beta-receptor antagonist, a calcium channel antagonist, a cell, a cell differentiation factor, a chemokine, a chemotherapeutic, a coenzyme, a cytotoxic agent, a prodrug of a cytotoxic agent, a cytostatic, an enzyme and its synthetic or biosynthetic analogue, a glucocorticoid, a growth factor, a haemostatic, a hormone and its synthetic or biosynthetic analogue, an immunosuppressant, an immunostimulant, a mitogen, a physiological or pharmacological inhibitor of mitogens, a mineralcorticoid, a muscle relaxant, a narcotic, a neurotransmitter, a precursor of a neurotransmitter, an oligonucleotide, a peptide, a para-sympathicomimetic, a para-sympatholytic, a protein, a sedating agent, a spasmolytic, a vasoconstrictor, a vasodilatator, a vector, a virus, a viral particle, a virustatic, a wound-healing substance, and combinations thereof; and a second mixing step of mixing the dry powder with an aqueous solution to form a paste or semi-solid material;

wherein the aqueous solution is gradually added to the dry powder in a total amount less than, equal to or equal to twice or in an amount at most equal to the total dry mass of the dry powder, wherein the ratio of the mass fraction of the aqueous solution to the dry powder is between 0.5 and 1, wherein at least a portion of the aqueous solution added in the second mixing step is gradually added to the dry powder during mechanical kneading.

15. A method for manufacturing a controlled-release drug-delivery composition, consisting of:

a first mixing step of mixing a dry powder consisting of a polymer, wherein the polymer is selected from the group consisting of polyvinyl alcohol (PVA), polyvinylpyrrolidone (PVP), polyethylene glycol (PEG), gelatin, collagen, alginate, starch, cellulose, chitosan, carboxymethylcellulose, cellulose derivatives, pectin, gum arabic, carrageenan, hyaluronic acid, albumin, fibrin, fibrinogen, synthetic polyelectrolytes, polyethylenimine, acacia gum, xanthan gum, agar agar, polyvinylalcohol, borax, polyacrylic acids, protaminsulfate, and casein;

a second mixing step of mixing the dry powder with an aqueous solution to form a paste or semi-solid material;

wherein the aqueous solution is gradually added to the dry powder in a total amount less than, equal to or equal to twice or in an amount at most equal to the total dry mass of the dry powder, wherein the ratio of the mass fraction of the aqueous solution to the dry powder is between 0.5 and 1;

wherein at least a portion of the aqueous solution added in the second mixing step is gradually added to the dry powder during the mechanical kneading; and a third mixing step of mixing a pharmaceutically active compound with the paste or semi-solid material to form a paste drug-delivery composition or semi-solid drug-delivery composition, wherein the pharmaceutically active compound is selected from the group consisting of antibody, immunoglobulins, fragments or fractions of immunoglobulins, synthetic substance mimicking immunoglobulins or synthetic, semisynthetic or biosynthetic fragments or fractions thereof, chimeric, humanized or human monoclonal antibodies, Fab fragments, fusion proteins or receptor antagonists, antiangiogenic compounds, intracellular signaling inhibitors, peptides having a molecular mass equal to or higher than 3 kDa, ribonucleic acids (RNA), desoxyribonucleic acids (DNA), plasmids, peptide nucleic acids (PNA), steroids, corticosteroids, an adrenocorticostatic, an antibiotic, an antidepressant, an antimycotic, a beta-adrenolytic, an androgen or antiandrogen, an antianemic, an anabolic, an anaesthetic, an analeptic, an antiallergic, an antiarrhythmic, an antiarterosclerotic, an antibiotic, an antifibrinolytic, an anticonvulsive, an antiinflammatory drug, an anticholinergic, an antihistaminic, an antihypertensive, an antihypotensive, an anticoagulant, an antiseptic, an antihemorrhagic, an antimyasthenic, an antiphlogistic, an antipyretic, a beta-receptor antagonist, a calcium channel antagonist, a cell, a cell differentiation factor, a chemokine, a chemotherapeutic, a coenzyme, a cytotoxic agent, a prodrug of a cytotoxic agent, a cytostatic, an enzyme and its synthetic or biosynthetic analogue, a glucocorticoid, a growth factor, a haemostatic, a hormone and its synthetic or biosynthetic analogue, an immunosuppressant, an immunostimulant, a mitogen, a physiological or pharmacological inhibitor of mitogens, a mineralcorticoid, a muscle relaxant, a narcotic, a neurotransmitter, a precursor of a neurotransmitter, an oligonucleotide, a peptide, a para-sympathicomimetic, a para-sympatholytic, a protein, a sedating agent, a spasmolytic, a vasoconstrictor, a vasodilatator, a vector, a virus, a viral particle, a virustatic, a wound-healing substance, and combinations thereof;

wherein the third mixing step consists of mechanical kneading.

* * * * *

UNITED STATES PATENT AND TRADEMARK OFFICE
CERTIFICATE OF CORRECTION

PATENT NO. : 9,474,715 B2  
APPLICATION NO. : 13/307474  
DATED : October 25, 2016  
INVENTOR(S) : Andreas Voigt et al.

It is certified that error appears in the above-identified patent and that said Letters Patent is hereby corrected as shown below:

In the claims

Column 14, Line 59 - "aqueous solution to form a paste or material," should be changed to "aqueous solution to form a paste or semi-solid material,"

Signed and Sealed this
Twentieth Day of December, 2016

Michelle K. Lee
*Director of the United States Patent and Trademark Office*